(12) United States Patent
Iwamoto (10) Patent No.: US 10,591,438 B2
(45) Date of Patent: Mar. 17, 2020

(54) GAS SENSOR ELEMENT AND MANUFACTURING METHOD THEREOF

(71) Applicant: DENSO CORPORATION, Kariya, Aichi-pref. (JP)

(72) Inventor: Yota Iwamoto, Kariya (JP)

(73) Assignee: DENSO CORPORATION, Kariya (JP)

( * ) Notice: Subject to any disclaimer, the term of this patent is extended or adjusted under 35 U.S.C. 154(b) by 447 days.

(21) Appl. No.: 15/323,210

(22) PCT Filed: Jun. 30, 2015

(86) PCT No.: PCT/JP2015/068889
§ 371 (c)(1),
(2) Date: Dec. 30, 2016

(87) PCT Pub. No.: WO2016/002807
PCT Pub. Date: Jan. 7, 2016

(65) Prior Publication Data
US 2017/0131229 A1    May 11, 2017

(30) Foreign Application Priority Data

Jun. 30, 2014 (JP) ................................. 2014-133483

(51) Int. Cl.
*G01N 27/407* (2006.01)
*G01N 27/403* (2006.01)
*G01N 33/00* (2006.01)

(52) U.S. Cl.
CPC ....... *G01N 27/4077* (2013.01); *G01N 27/407* (2013.01); *G01N 27/4035* (2013.01);
(Continued)

(58) Field of Classification Search
CPC .. G01M 15/10; G01M 15/102; G01M 15/104; G01N 27/404–407;
(Continued)

(56) References Cited

U.S. PATENT DOCUMENTS 5,948,225 A † 9/1999 Katafuchi
6,254,926 B1   7/2001 Katafuchi et al.
(Continued)

FOREIGN PATENT DOCUMENTS

JP    58-100746    6/1983
JP    61-155267    7/1986
(Continued)

OTHER PUBLICATIONS

English Machine Translation of JPS58100746 (Year: 1983).*

*Primary Examiner* — Gurpreet Kaur
(74) *Attorney, Agent, or Firm* — Nixon & Vanderhye P.C.

(57) ABSTRACT

A gas sensor element with excellent sensor output reliability and durability and a manufacturing method thereof is provided. The gas sensor element is provided with an oxygen-ion conductive solid electrolyte body, a measuring electrode and a reference electrode provided respectively on surface and another surface of the solid electrolyte body, a signal lead part 5 connected to the measuring electrode, which also extends to a base end side thereof, a first ceramic layer covering the signal lead part from an opposing side to the solid electrolyte body, and a second ceramic layer intervening between the signal lead part and the solid electrolyte body. The signal lead part is formed from one metal or an alloy of more than one metal selected from a group consisting of Pt, Au, Ag, Pd, Rh, Ni and Ir. On the second ceramic layer, a dyeing section which is the metal or an alloy of more than one metal dyed thereon, is formed from the signal lead part side.

20 Claims, 8 Drawing Sheets

(52) U.S. Cl.
CPC ..... *G01N 27/4071* (2013.01); *G01N 27/4075* (2013.01); *G01N 33/0036* (2013.01)

(58) Field of Classification Search
CPC .... G01N 27/409; G01N 27/419; G01N 27/41; F01N 2560/00–20; F01N 2550/00–24
See application file for complete search history.

(56) References Cited

U.S. PATENT DOCUMENTS

| | | | |
|---|---|---|---|
| 2002/0160102 | A1† | 10/2002 | Kozaki |
| 2008/0264146 | A1† | 10/2008 | Roesch |
| 2013/0019655 | A1† | 1/2013 | Nakagawa |
| 2013/0306475 | A1 | 11/2013 | Suzuki et al. |

FOREIGN PATENT DOCUMENTS

| | | |
|---|---|---|
| JP | 61-254848 | 11/1986 |
| JP | 63-256588 | 10/1988 |
| JP | 3-142353 | 6/1991 |
| JP | 11-326267 | 11/1999 |
| JP | 2000-081411 | 3/2000 |
| JP | 2010-117348 | 5/2010 |

\* cited by examiner
† cited by third party

GAS SENSOR ELEMENT AND MANUFACTURING METHOD THEREOF

CROSS REFERENCE ASSOCIATED APPLICATION

This application is the U.S. national phase of International Application No. PCT/JP2015/068889 filed on Jun. 30, 2015, and claims priority to Japanese Patent Application No. 2014-133483 filed on Jun. 30, 2014, the entire contents of each of which are hereby incorporated herein by reference.

TECHNICAL FIELD

The present disclosure relates to a gas sensor element provided in a gas sensor, for the detection of a concentration of a specific gas in a gas to be measured, and a manufacturing method for manufacturing the gas sensor element.

RELATED ART

In an exhaust system of a combustion engine of a vehicle, for example, a gas sensor is mounted to detect a concentration of a specific gas (such as an oxygen concentration) in a measuring gas of an exhaust gas, and the like.

In this type of gas sensor, a gas sensor element built in the gas sensor, has an oxygen-ion conductive solid electrolyte body, and a measuring gas measuring electrode and a reference electrode provided on one side and another side of the solid electrolyte body.

There is a gas sensor element having one end of a signal lead part connected to a measuring electrode extending to a base end-side thereof (for example, refer to Patent literature 1). The gas sensor element has a first ceramic layer covering an opposing side to the solid electrolyte body in order to protect the signal lead part. Additionally, a second ceramic layer intervenes between the signal lead part and a solid electrolyte body to prevent an oxygen-ion current from leaking. The signal lead part is thus formed from a platinum paste on a surface of a second ceramic layer.

CITATION LIST

Patent Literature

[Patent Literature 1] JP 2013-238556 A.

SUMMARY OF INVENTION

Technical Problem

However, when there is need for a sensor with a high sensor output reliability, it can be difficult to meet such needs with a gas sensor element having the signal lead part made from the platinum paste. That is, since the platinum paste is a mixture of platinum and a binder, an electrical resistance is high and variation of the electrical resistance easily increases due to unevenness of impurities, such as the binder. Also, it is difficult to increase the sensor output reliability of the gas sensor element as the electrical resistance of the signal lead part is high and also highly variable.

In view of the above circumstances, by forming a signal lead part from pure platinum, sensor output reliability can be improved. However it still remains difficult to secure adhesion of the signal lead part to a second ceramic layer, when the signal lead part made from pure platinum is formed on a surface of the second ceramic layer. As a result, durability of the gas sensor element is difficult to secure.

The present disclosure has taken the above into account and strives to provide a gas sensor with a superior sensor output reliability and durability, and also a manufacturing method thereof.

Solution to Problem

A mode of the present disclosure is gas sensor element provided with an oxygen-ion conductive solid electrolyte body, a measuring electrode and a reference electrode mounted respectively on a surface and another surface of the solid electrolyte body, a signal lead part electrically connected to the measuring electrode which also extends to a base end-side thereof, a first ceramic layer covering the signal lead part from an opposing side to the solid electrolyte body and a second ceramic layer intervening between the signal lead part and the solid electrolyte body. The lead part is made from any one metal or an alloy of more than one metal, selected from a group consisting of Pt, Au, Ag, Pd, Rh, Ni and Ir. On the second ceramic layer, a dyeing section dyed with the metal or the alloy of more than one metal, is formed from the signal lead part side.

Another mode of the present disclosure, is a method to manufacture the gas sensor element provided with the oxygen-ion conductive solid electrolyte body, the measuring electrode and the reference electrode mounted respectively on the surface and the other surface of the solid electrolyte body, the signal lead part electrically connected to the measuring electrode and also extends to the base end side thereof, the first ceramic layer covering the signal lead part from an opposing side to the solid electrolyte body and the second ceramic layer intervening between the signal lead part and the solid electrolyte body. In forming the signal lead part the one metal or the alloy of more than one metal selected from a group consisting of Pt, Au, Ag, Pd, Rh, Ni and Ir is deposited on an outer surface of the second ceramic layer by electroless plating.

The gas sensor element is provided with the signal lead part section made of one metal or the alloy of more than one metal selected from the group consisting of Pt (platinum), Au (gold), Ag (silver), Pd (palladium), Rh (rhodium), Ni (nickel), and Ir (iridium). More specifically, the signal lead part 5 is formed from platinum which substantially has no inclusion of impurities, and is not formed from a metal or an alloy of more than one metal such as a platinum paste combined with other materials. An electrical resistance of the signal lead part 5 can thus be decreased, resulting in an improved sensor output reliability of the gas sensor element.

On the second ceramic layer, a platinum dyed dyeing section is formed from the signal lead part side. As a result, the adhesion of the signal lead part on the second ceramic layer can be improved. More specifically, the dyeing section is an area dyed with a metal or an alloy of more than one metal, which forms the signal lead part from the signal lead part to the second ceramic layer, exerting a so called 'anchor effect'. In turn, adhesion strength between the signal lead part and the second ceramic layer is thus ensured, and a gas sensor element having superior durability can be obtained.

In this way, by forming the signal lead part from the metal or the alloy of more than one metal, the gas sensor element enables a decrease in variation of the electrical resistance of the signal lead part, on the other hand, the anchor effect of the dyeing section also secures the adhesion strength of the signal lead part to the second ceramic layer.

Regarding the manufacturing method for the gas sensor element, the signal lead part is formed by electroless plating. That is, when the signal lead part is formed, a layer of metal or the alloy of more than one metal is deposited on the outer surface of the second ceramic layer provided on an outer side of the electrolyte body, using an electroless plating method. At this point, a plating solution is permeated into pores of an inner-part of the second ceramic layer. The dyeing section thus provides an anchor for the signal lead part. As a result, the gas sensor element becomes a sensor element with durability.

A described above, according to the present disclosure, the gas sensor element having excellent sensor output reliability and durability, in addition to the manufacturing method thereof can be provided.

BRIEF DESCRIPTION OF DRAWINGS

In the accompany drawings.

DESCRIPTION OF EMBODIMENTS

A gas sensor element, for example is built in a gas sensor mounted on an exhaust system of a combustion engine of a vehicle. The gas sensor element, for example, may be employed as an air-fuel (A/F) sensor to detect an air-fuel ratio (A/F) of a mixed gas supplied to the combustion engine based on a limiting current flowing between electrodes, which is dependent on a concentration of a specific gas (oxygen) in a measuring gas (exhaust gas). The gas sensor element may also be used as an oxygen sensing element to detect an air-fuel ratio based on an electromotive force occurring between electrodes which is dependent on a ratio between a specific gas concentration (oxygen concentration) in a measuring gas (exhaust gas) and in a reference gas (atmosphere).

The gas sensor element may also be, for example, configured as a cup shaped gas sensor with a closed front end-side and an open base end-side solid electrolyte body provided therein.

Additionally, the gas sensor element may be a laminated gas sensor configured having a plate-shaped solid electrolyte body with other ceramic layers laminated in a thickness direction thereof.

It is noted that, in the present specifications, an end of the gas sensor which introduced in an exhaust system, for example, with the gas sensor element built therein, is referred to as a 'front end' and an opposing side referred to 'a base end'.

A dyeing depth which is a depth of a dyeing section, from the surface of the signal lead part-side of the second ceramic layer, is preferably 0.2 µm or more. In this case, an anchor effect of the dyeing section is sufficiently obtained and a durability of the gas sensor element can be further improved.

A distance between a boundary surface and the dyeing section is preferably 5 µm or more. The boundary surface refers to a surface between the second ceramic layer and the solid electrolyte. In this case, a preventive effect of an oxygen-ion current leaking from between the signal lead part of the second ceramic layer and solid electrolyte body can be sufficiently ensured. As a result, a gas sensor element having high sensing output reliability can be obtained.

The signal lead part is made from any one metal or an alloy of more than one metal consisting of Pt, Au, Ag, Pd, Rh, Ni or Ir. More specifically, the signal lead part is not made from a mixture of other materials and the metal or the alloy of more than one metal. This does not, however, exclude a small amount of other impurities contained in the signal lead part. A purity of the metal or the alloy of more than one metal of the signal lead part is preferably 90 mass percent or more. In which case, the sensor output reliability of the gas sensor element 1 can be effectively improved.

First Embodiment

Accompany FIGS. 1 to 7 of the embodiments for the gas sensor element 1 will be described.

Figure 1:
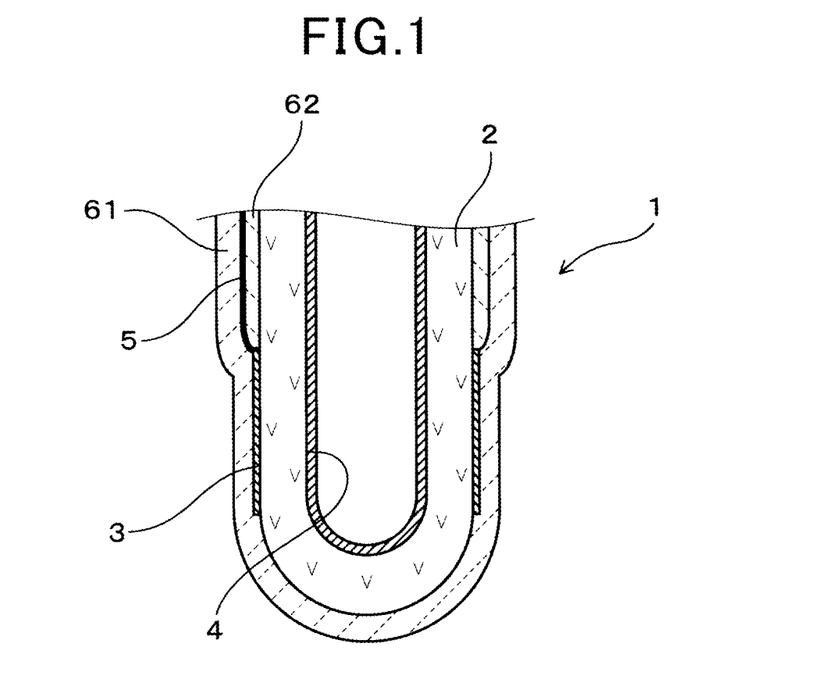
FIG. 1 shows a cross sectional view of a front end section of a gas sensor element according to a first embodiment.

A gas sensor element 1 in the first embodiment is provided with an oxygen-ion conductive electrolyte body 2, a measuring electrode 3 and a reference electrode 4 provided respectively on a surface and another surface of the oxygen-ion conductive solid electrolyte 2. Additionally, the gas sensor element 1 is provided with a signal lead part 5 connected to the measuring electrode 3 which also extends to a base end-side thereof, a first ceramic layer 61 which covers the signal lead part 5 from a side opposite to the solid electrolyte body 2, and a second ceramic layer 62 mounted between the signal lead part 5 and the solid electrolyte body 2.

Figure 4:
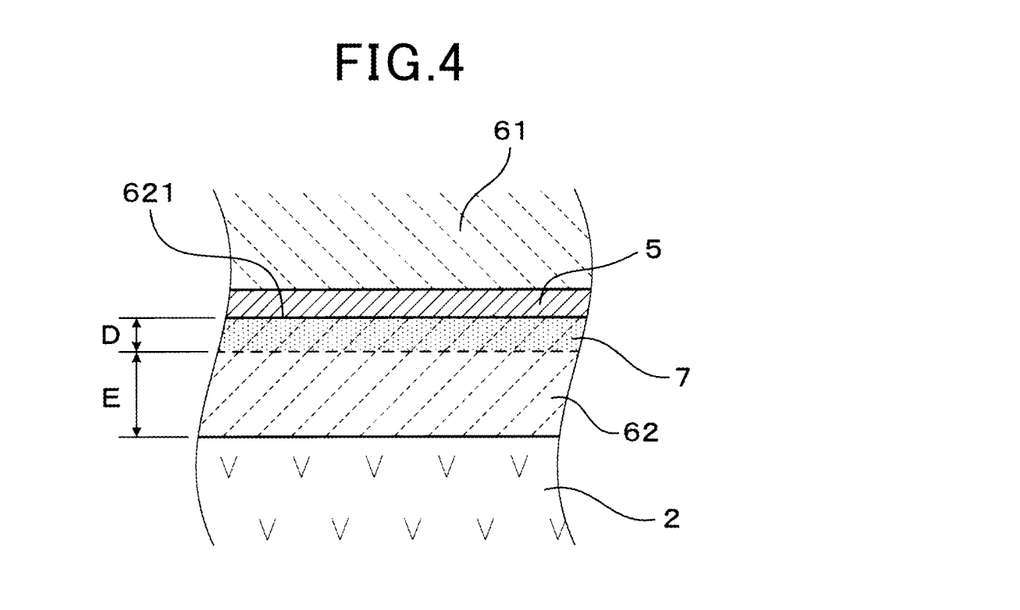
FIG. 4 shows a cross sectional enlargement of a vicinity of a dyeing section according to the first embodiment.

The signal lead part 5 is made from any one metal or an alloy of more than one metal consisting of Pt, Au, Ag, Pd, Rh, Ni or Ir. In the first embodiment, the signal lead part 5 consists of Pt (platinum). As shown in FIG. 4, on the second ceramic layer 62, a dyeing section 7 dyed with the metal or the alloy of more than one metal (in the present embodiment platinum) is formed from the signal lead part 5-side.

The signal lead part 5 is made from pure platinum containing no impurities, other than inevitable impurities, the platinum purity of the signal lead part 5 being 90 mass percent or more.

Figure 2:
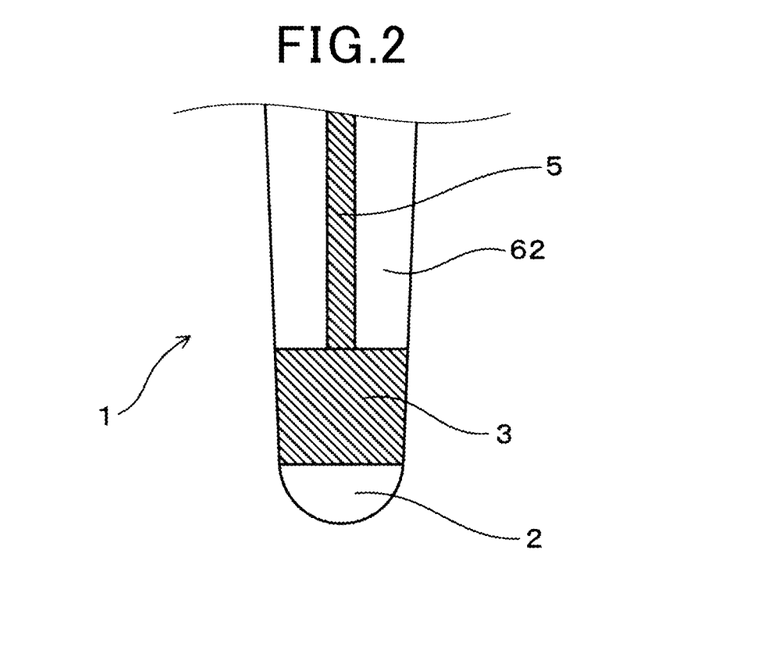
FIG. 2 shows a front view of the front section of the gas sensor element without a first ceramic layer according to the first embodiment.

The gas sensor element 1, according to the first embodiment, is a cup shaped gas sensor element having a cup shaped solid electrolyte body 2 with a closed front end and an open base end provided therein, as shown in FIGS. 1 and 2. The solid electrolyte body 2 is formed from zirconia ($ZrO_2$) as a major substance. The reference electrode 4 is formed on an inner side of the cup-shaped solid electrolyte body 2, and the measuring electrode 3 is formed on an outer side of thereof. The measuring electrode 3 and the reference electrode 4 are both made of platinum.

The reference electrode 4 is formed substantially on all of the total inner side of the solid electrolyte body 2. On the other hand, the measuring electrode 3 is provided on a section around a front end area of the solid electrolyte body 2. In the first embodiment, a front end of the measuring electrode 3 is, however, positioned closer to at a base end-side of the sensor element 1, with respect to the front end of the solid electrolyte body 2. The measuring electrode 3 is formed in a total circumferential direction thereof.

Figure 5:
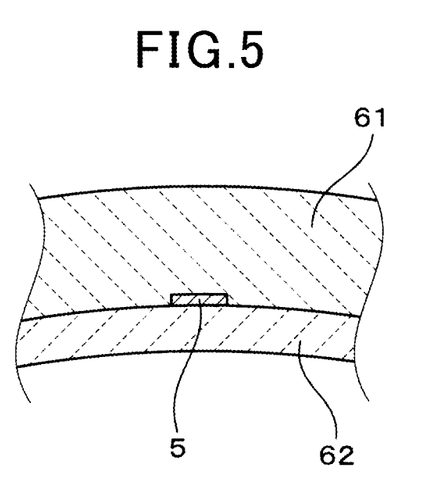
FIG. 5 shows a cross sectional view of the signal lead, the first ceramic layer and a second ceramic layer taken across a line V-V shown in FIG. 3, according to the first embodiment.

Still referring to FIG. 2, the signal lead part 5 is formed on the outer side of the solid electrolyte body 2, stretching from a base end of the measuring electrode 3 to a base end side thereof. The signal lead part 5 is formed in a section of the second ceramics layer 62, in a width direction of the signal lead part 5, as shown FIG. 2 and FIG. 5. Specifically, the signal lead part 5 is formed in one section only of the solid electrolyte body 2, in a circumferential direction thereof. The first ceramic layer 61 and the second ceramic layer 62 are formed completely around the circumference of the solid electrolyte body 2. For this reason, the first ceramic layer 61 and second ceramic layer 62 are closely fixed to each other in areas where the signal lead part 5 is not formed, as shown in FIG. 5.

The second ceramic layer 62 provided between the solid electrolyte body 2 and the signal lead part 5 is a dense ceramic layer having alumina ($Al_2O_3$) or spinel ($MgAl_2O_4$) as a major component. A porosity of the second ceramic layer 62 is in a range of 1 to 20%. The second ceramic layer 62 is mounted substantially on a total outer side of the solid electrolyte body 2, at a base end-side thereof, with respect to the measuring electrode 3. A thickness of the second ceramic layer 62 is in a range of 5.2 μm to 200 μm.

The first ceramic layer 61 is formed substantially on the total outer side of the solid electrolyte body 2, covering the signal lead part 5 and the measuring electrode 3 from an outside thereof. The first ceramic layer 61 is also formed from alumina as a major component. The first ceramic layer 61 is formed to cover the measuring electrode 3, and configured so that a measuring gas around the gas sensor element 1 penetrates through the first ceramic layer 61 to reach the measuring electrode 3. The porosity of the second ceramic layer 62 is in a range of 1 to 20%.

The first ceramic cover 61 protects the measuring electrode 3 and the signal lead part 5 from heat, for example, from the measuring gas, without shielding a supply of the measuring gas to the measuring electrode 3, and prevents the aggregation of platinum which forms the measuring electrode 3 and the signal lead part 5.

Figure 3:
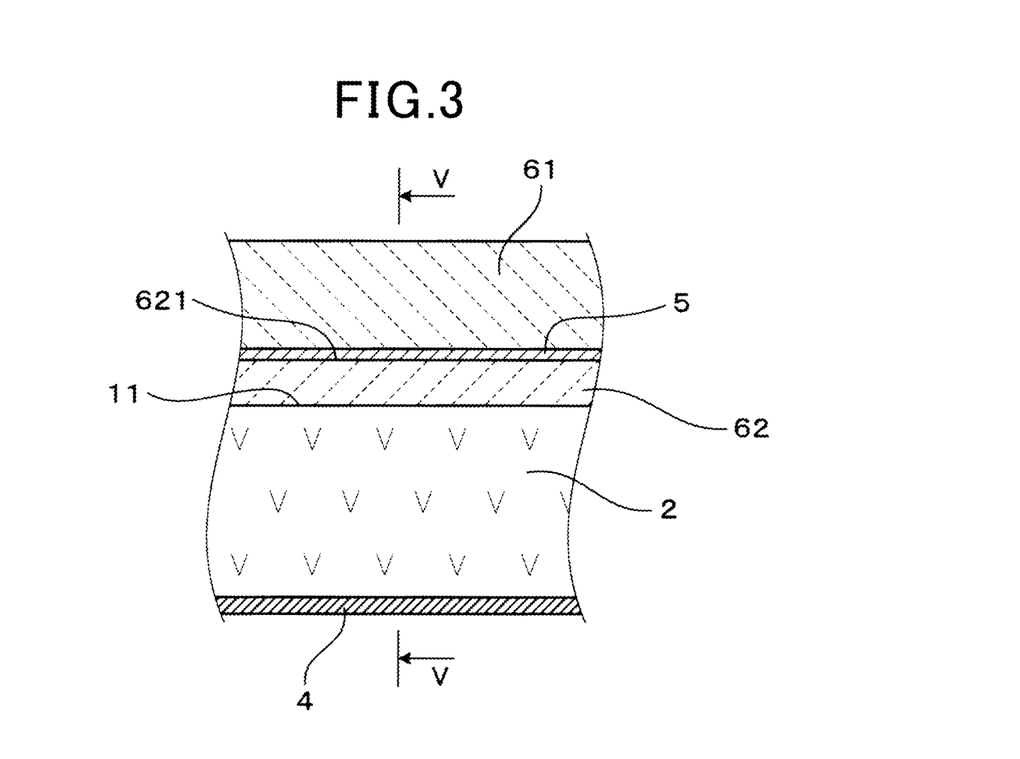
FIG. 3 shows a planar cross sectional view including a central axis of the gas sensor element around a signal lead part according to the first embodiment.

The signal lead part 5 is provided on an outer surface 621 of the second ceramic layer 62, as shown in FIG. 1 and FIG. 3. Furthermore, a dyeing depth D which is a depth of a dyeing section 7 from a surface (outer surface 621) of the signal lead part 5-side of the second ceramic layer(62) is 0.2 μm or more, as shown in FIG. 4. A distance E between a boundary surface 11 of the second ceramic layer 62 and the solid electrolyte body 2, and the dyeing section 7, is 5 μm or more.

The dyeing section 7 is formed by a state of permeating platinum into pores of the second ceramic layer 62, from an outer surface 621 of the second ceramic layer 62. More specifically, as shown FIGS. 6A and 6B, a plurality of platinum can be observed in a position near to the outer surface 621 of the second ceramic layer 62, when the gas sensor element 1 is observed by electron microscope (SEM), as a flat parallel cross cut section of the second ceramic layer 62 and the signal lead part 5 in a parallel direction thereof. A part where the platinum resides is the dyeing section 7. In FIG. 6B, platinum is shown shaded.

Figure 6A:
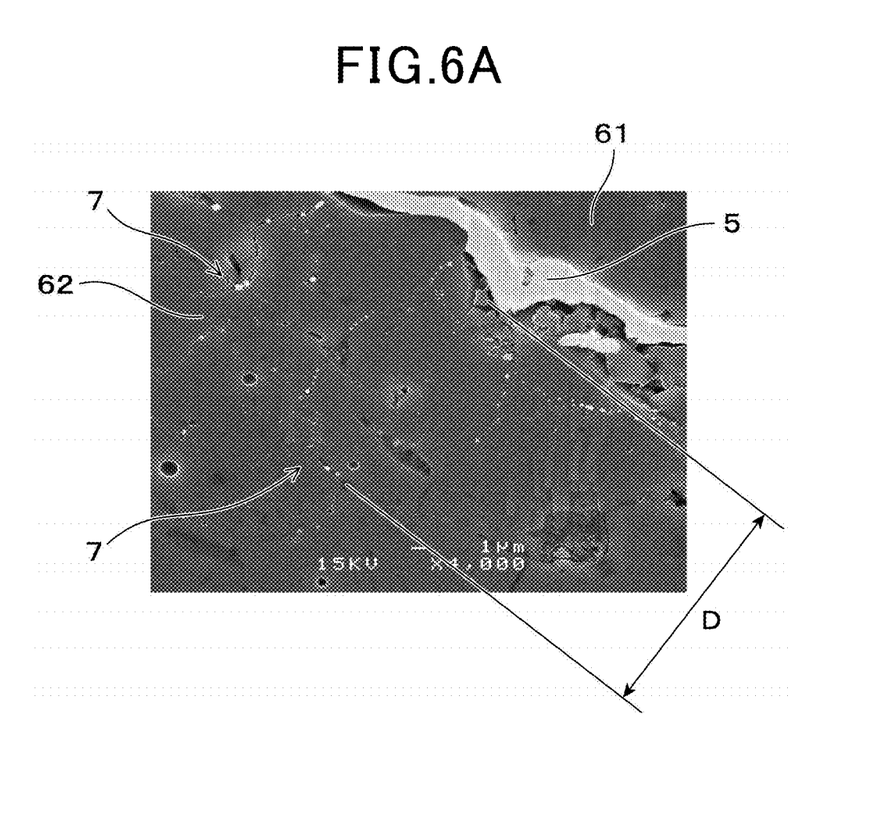
FIG. 6A shows an electron microscopy photographic-image of a cross section of the signal lead part and a vicinity of the dyeing section (4000 times magnification) according to the first embodiment.
Figure 6B:
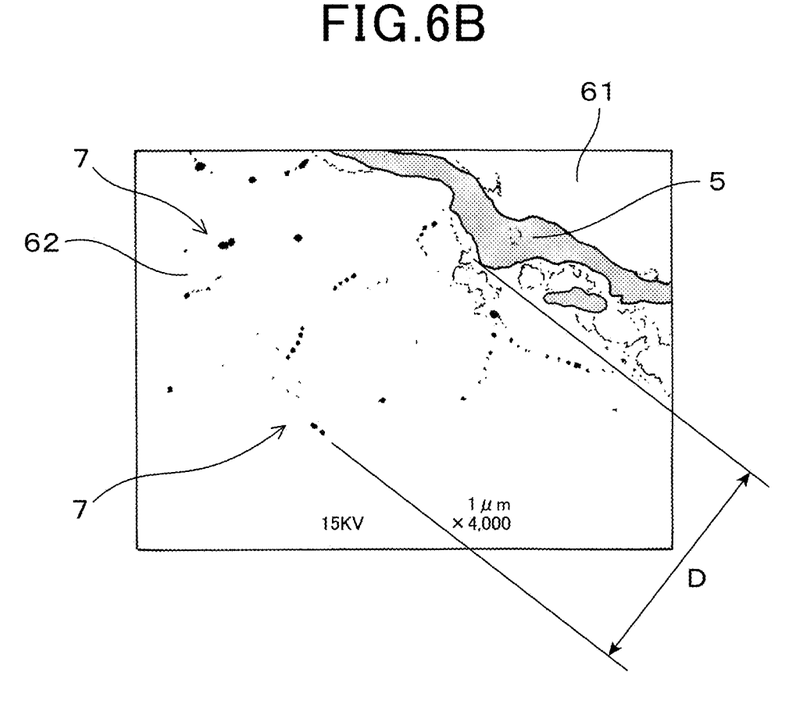
FIG. 6B shows a featured area of an electron microscopy photographic-image of a cross section of the signal lead part and a vicinity of the dyeing section when subjected to Pt dyeing (4000 times magnification) according to the first embodiment.

As shown in FIGS. 6A, 6B, 7A and 7B, the outer surface 621 of second ceramic layer 62 has a concave-convex shape and the signal lead part 5 is waved in a thickness direction thereof. The dyeing depth D is defined as depth toward a perpendicular direction of each part of the signal lead part 5 (outer surface 621) as shown in FIG. 6A and FIG. 6B, which is not necessarily the same as a depth of a lamination direction of the solid electrolyte body 2, the second ceramic layer 62 and the signal lead part 5 respectively (refer to "top to bottom direction" FIG. 7A and FIG. 7B).

Figure 7A:
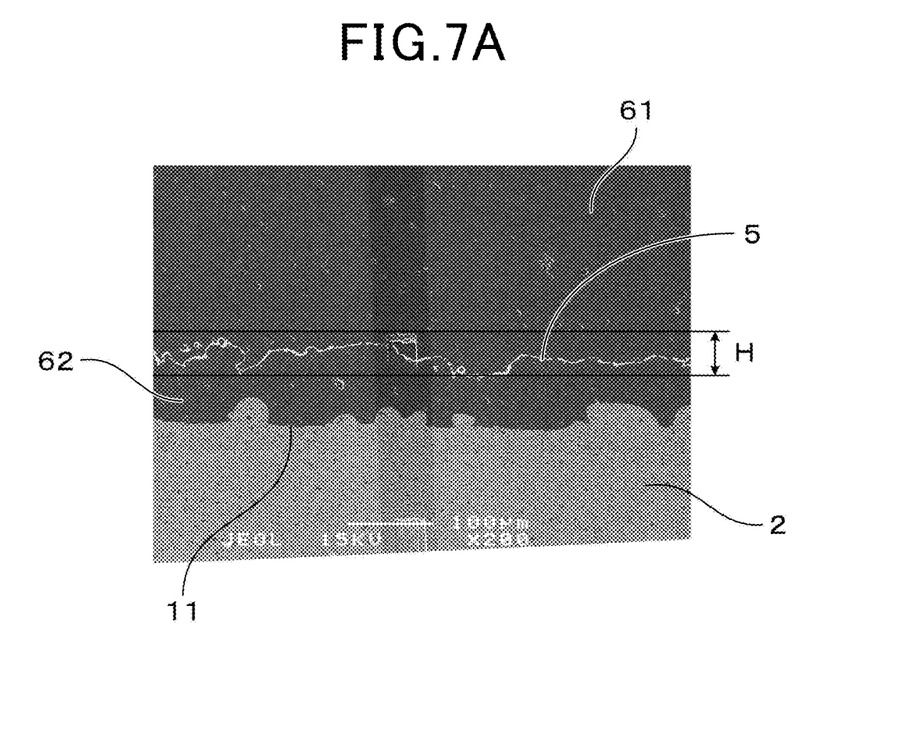
FIG. 7A shows an electron microscopy photographic image of a cross section of the signal lead part (200 times magnification) according to the first embodiment.
Figure 7B:
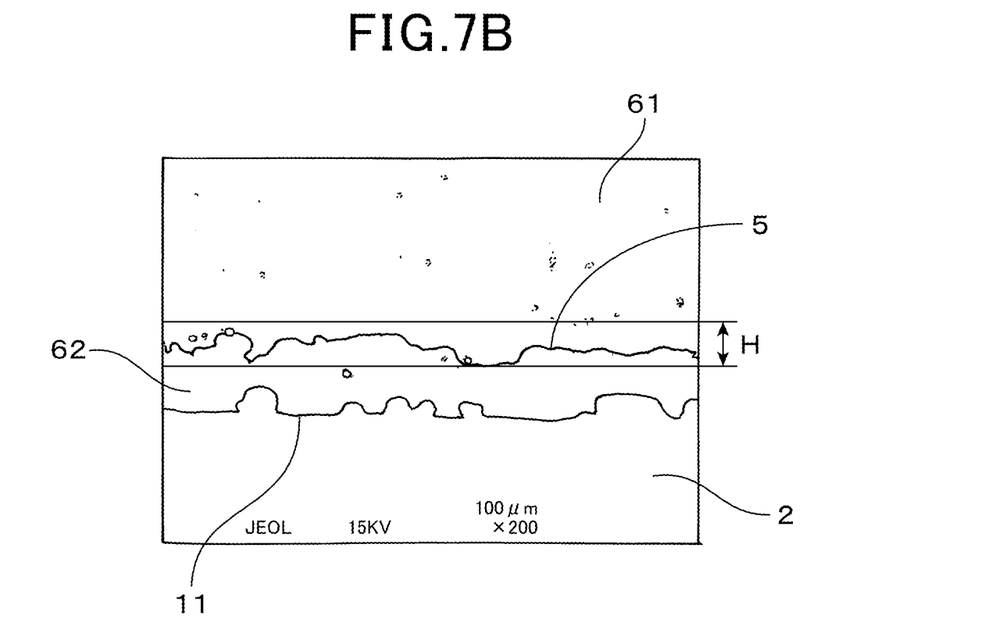
FIG. 7B shows a featured area of an electron microscopy photographic image of a cross section of the signal lead (200 times magnification) according to the first embodiment according to the first embodiment.

As shown in FIG. 7A and FIG. 7B, a wave of the signal lead part 5 waves along a thickness region H of 5 μm to 200 μm, as a thickness in a laminated direction of the solid electrolyte body 2, the second ceramic layer 62 and the signal lead part 5. Due to the waves of the signal lead part 5, the signal lead part 5 is clamped with a high adhesion strength between the second ceramic layer 62 and the first ceramic layer 61, and aggregation of a metal (platinum) configuring the signal lead part 5 is prevented.

The signal lead part 5 is formed from a plating method. More specifically, an electroless plating method is used when the signal lead part 5 is formed. At this stage, a platinum layer is laminated on the outer surface 621 of the second ceramic layer 62, provided on the outer surface of the electrolyte body 2. When the deposition is performed, a depositing solution is permeated into the pores of the second ceramic layer 62 from the outer surface 621 thereof. As a result, the signal lead part 5 made from platinum is formed on the outer surface 621 of the second ceramic layer 62, and the dyeing section 7 is formed on an inner part of the second ceramic layer 62. For this reason, the platinum forming the dyeing section 7 is connected to the platinum forming the signal lead part 5 and the dyeing section 7 serves as an anchor of the signal lead part 5.

A thickness of the signal lead part 5 ranges from 0.5 μm to 10 μm. The thickness of the second ceramic layer 62 ranges from 5.2 μm to 100 μm.

The gas sensor element 1 is built into a gas sensor mounted on an exhaust gas system of a combustion engine (un-shown). The gas sensor element 1, according to the first embodiment, is a limiting current-type gas sensor element which outputs a limiting current value dependent on a concentration of a specific gas (oxygen) in a measuring gas, by applying a predesignated voltage between the measuring electrode 3 and the reference electrode 4.

The gas sensor element 1, for example, can be a gas sensor element built into a rear gas sensor, mounted downstream, with respect to a catalyst filer in an exhaust system of the internal combustion engine. More specifically, the gas sensor with the inbuilt gas sensor element 1 can be mounted down-stream with respect to a catalyst filter which purifies exhaust gas, on the exhaust system of an automotive engine. In this case, the limiting current value dependent on the oxygen concentration in the exhaust gas is output after passing through the catalyst filter. Additionally, the gas sensor can be configured so that the air-fuel ratio of the mixture supplied to the internal engine is calculated based on an acquired limiting current value and there is a feedback to an engine control system. The present disclosure is however not limited to the gas sensor element 1 described above and various modes may be employed.

A working effect of the example will now be described.

The gas sensor element 1 is provided with the signal lead part 5 made from platinum. More specifically, the signal lead part 5 is formed from platinum which substantially has no inclusion of impurities, and not formed from platinum such as a platinum paste for example, mixed with other materials (binder and the like). An electrical resistance of the signal lead part 5 can be thus decreased, resulting in an improved sensor output reliability of the gas sensor element 1.

Conventionally, when a signal lead part is made from a platinum paste, an electrical resistance of 15 to 25 $\mu\Omega$/cm for example, can be reduced to 9 to 11$\mu\Omega$/cm with the signal lead part 5 formed from platinum according to the first embodiment. Furthermore, variation of resistance values can also be decreased, resulting in a signal lead part 5 with a reduced resistance, and improved sensor output precision due to the reduced variation.

Since the dyeing section 7 is formed on the second ceramic layer 62, adherence of the signal lead part 5 to the second ceramic layer 62 can be improved. More specifically, the dyeing section 7 is a layer of platinum dyed thereon from the signal lead part 5 to the second ceramic layer 62, in which a so called 'anchor effect' is exerted. The adhesion strength between the signal lead part 5 and the second ceramic layer 62 is thus ensured and the gas sensor element 1 having excellent durability can be obtained.

In this way, a reduction of the resistance variation of the signal lead part 5 is achieved, as the signal lead part 5 is formed from platinum, and the adhesion strength of the signal lead part 5 to the second ceramic layer 62 is ensured by the anchor effect of the dyeing section 7.

Furthermore, since the dyeing depth D of the dyeing section 7 is 0.2 µm or more, the anchor effect of the dyeing section 7 is sufficiently exerted, and the durability of the gas sensor element 1 can be further improved.

Also, the distance E between the boundary surface 11 of the second ceramic layer 62 and the solid electrolyte body 2, and the dyeing section 7 is 5 µm or more. As a result, effective prevention of oxygen-ion leakage from between the signal lead part 5 of the second ceramic layer 62 and the solid electrolyte body 2 is ensured. The gas sensor element 1 having high gas sensor output reliability can be ensured.

According to the exemplary embodiment, a gas sensor element with sensor output reliability and excellent durability and a manufacturing method thereof can be provided.

Second Embodiment

Figure 8:
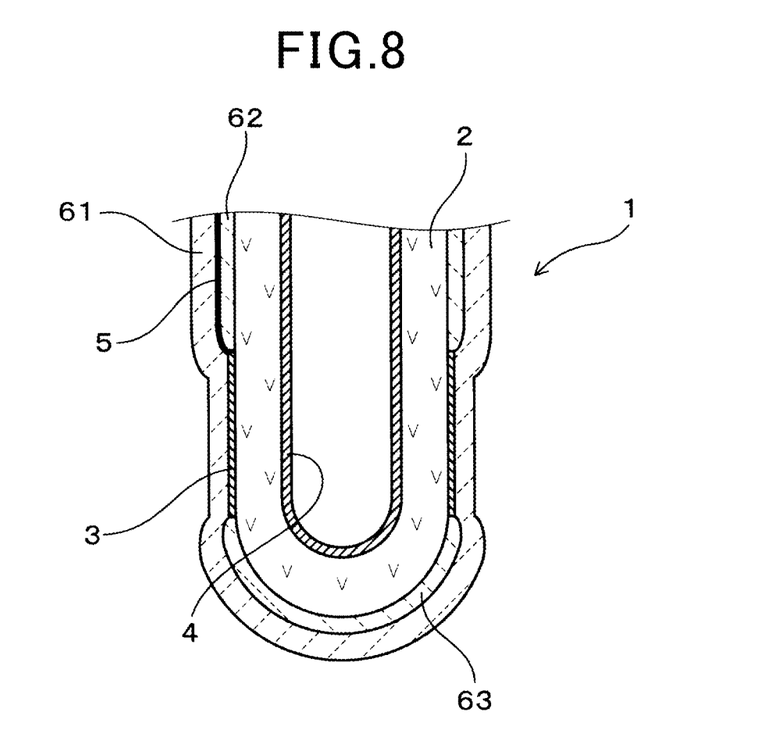
FIG. 8 is a cross section of the front end section of the gas sensor element according to the second embodiment.

A second embodiment, is an example of a third ceramic layer 63 provided on a front end-section of the solid electrolyte body 2 of a gas sensor element 1, as shown in FIG. 8.

The third ceramic layer 63 has a structure, material and thickness, for example, that is the same as the second ceramic layer 62. The third ceramic layer 63 is formed on a front end side region on the outer surface of the solid electrolyte body 2, with respect to the measuring electrode 3.

Other features of the gas sensor element 1 in the second embodiment are the same as the first embodiment. Unless shown otherwise, symbols used in the present embodiment or in the figures of the present embodiment are the same as the symbols used to represent the elements configuring the first embodiment.

In the second embodiment, configuration of the measuring electrode 3 relative to the solid electrolyte body 2 can be achieved more precisely. Specifically, in forming the measuring electrode 3, the second ceramic layer 62 and the third ceramic layer 3 are formed on the outer surface of the solid electrolyte body 2. Thereafter, the measuring electrode 3 is formed in a region surrounding the second ceramic layer 62 and the third ceramic layer 63 of the outer surface of the solid electrolyte body 2. As a result, the measuring electrode 3 can be formed precisely in a predetermined position of the solid electrolyte 2. Other working effects are the same as the first embodiment.

Experiment Example 1

Experiment example 1 verifies a relation of the dyeing depth D of the dyeing section 7 and durability of the signal lead part, referring to Table 1.

When a test was performed, a plurality of gas sensor elements each having a different dyeing depth D were mounted in a gas sensor. A gas sensor element without a dyeing depth 7 was also evaluated in the same way. Additionally, 4 samples were prepared for each standard. A basic structure of the gas sensor element is the same as the structure of the gas sensor element 1 in the first embodiment. It is noted that, unless shown otherwise, symbols used in the present example or in the FIGS. of the present example are the same as the symbols used to represent the configuring elements of the first embodiment.

Each sensor was set in an exhaust pipe of a gasoline engine, a fully opened accelerator state and idling state were repeatedly performed every 10 minutes, and approximately a 3000 hour durability test was performed. It is noted that, in the fully opened accelerator state a temperature of the gas sensor element reached 1000° C., and in the idling state a heater was adjusted so that the gas sensor element reached 300° C.

Before and after the durability test, the resistance of each signal lead part of each gas sensor element was measured and a change in the resistance was evaluated. The results are shown in Table 1.

TABLE 1

| | Dyeing depth D [µm] | | | | |
|---|---|---|---|---|---|
| | 0 | 0.1 | 0.2 | 0.3 | 0.5 |
| Evaluation | B | B | A | A | A |
| | B | B | A | A | A |
| | B | A | A | A | A |
| | B | A | A | A | A |

In Table 1 [A] represents an electrical resistance changing ratio of less than 10%, which is evaluated as having sufficient durability. On the other hand, [B] represents the electrical resistance changing ratio of 10% or more. It is clear from FIG. 1, that the electrical resistance changing ratio of anyone of the four samples without the dyeing section 7 (the dyeing section which has a dyeing depth D of 0 µm) is 10% or more. On the hand, samples having the dyeing section 7 showed an improved electrical resistance changing ratio, in particular, the electrical resistance changing ratio of all samples with a depth of 0.2 µm or more was decreased to less than 10%, thus it is clear that the durability of signal lead part 5 is of superior quality.

Experiment Example 2

Experiment example 2 is an experiment which verifies leakage of the oxygen-ion current between the boundary surface 11 of the second ceramic layer 52 and the solid electrolyte body 2, and the distance E of the dyeing section 7, and also between the signal lead part 5 and the solid electrolyte body 2.

When a test was performed, a plurality of gas sensor elements having a different distance E were mounted in each gas sensor and the gas sensor equipped with the sensor element, having a different distance E, was used in the test. A gas sensor element (E=0) with the dyeing section 7 reaching the boundary surface 11 was evaluated in the same manner. Four samples were prepared for each standard. A basic structure of the gas sensor used in the test was the same as the gas sensor element 1 in the first embodiment. It is noted that, unless shown otherwise, symbols used in the example or in the figures of the example are the same as the symbols used for the configuring elements in the first embodiment.

In performing the test, a limiting current value obtained as the sensor output was measured in each of the gas sensors measuring a plurality of different types of exhaust gases having an air-fuel ratio which is present in a range of ratios 13 to 18. A maximum/minimum difference for the limiting current value that is ideally obtained was evaluated for each exhaust gas of each air-fuel ratio. If the difference of limiting current value is large (stoichiometry precision is low) it is considered that an oxygen-ion leak is occurring between the signal lead part 5 and the solid electrolyte body 2. In other words, if a leak occurs, the measured limiting current value will increase by an amount that has leaked. The evaluation results are shown in Table 2.

TABLE 2

| | Distance [μm] | | | | |
|---|---|---|---|---|---|
| | 0 | 3 | 4 | 5 | 6 |
| Evaluation | B | B | B | A | A |
| | B | B | A | A | A |
| | B | B | A | A | A |
| | B | A | A | A | A |

In table 2, [A] represents a sample with a difference of less than 10%, which is evaluated as having sufficient output reliability. On the other hand [B] represents a sample with a difference of 10% or more. It is clear from Table 2 that the limiting current value difference is decreased to less than 10% for all samples having the distance E of 5 μm or more. In this regard, from the results, it is clear that a leak of the oxygen-ion current between the signal lead part 5 and solid electrolyte body 2 can be sufficiently prevented.

In the present embodiment, a bottomed-cylindrical cup shaped gas sensor element was described, however, the presented disclosure may be adapted to a gas sensor element made from a plate-shaped electrolyte body having other layers laminated thereon.

Additionally, in the present embodiment, a signal lead part formed from platinum is exemplified, however, the signal lead part is not limited to be formed from platinum and may be formed from a metal or the alloy of more than one metal selected from Pt, Au, Ag, Pd, Ag, Pd, Rh, Ni and Ir, or made from another material.

REFERENCE SIGN LIST

1 gas sensor element, 2 solid electrolyte body, 3 measuring electrode, 4 reference electrode, 4 signal lead part, 61 first ceramic layer, 62 second ceramic layer, 63 third ceramic layer, 7 dyeing section.

What is claimed is:

1. A gas sensor element wherein the gas sensor element comprises;
    an oxygen-ion conductive solid electrolyte body;
    a measuring electrode and a reference electrode provided respectively on a surface and another surface of the oxygen-ion conductive solid electrolyte body;
    a signal lead part connected to the measuring electrode, the signal lead part extending to a base end side of the measuring electrode;
    a first ceramic layer covering the signal lead part from an opposing side to the solid electrolyte body; and
    a second ceramic layer mounted between the signal lead part and the solid electrolyte body,
    wherein:
    the signal lead part is made from any one metal or an alloy of more than one metal selected from a group consisting of Pt, Au, Ag, Pd, Rh, Ni and Ir, and
    the second ceramic layer has formed therein a dyeing section abutting the signal lead part, and
    the dyeing section comprising a part of the metal or the alloy that has been dyed in the second ceramic layer.

2. The gas sensor element according to claim 1, wherein a dyeing depth which is the depth of the dyeing section from a surface side of the signal lead part of the second ceramic layer is 0.2 μm or more.

3. The gas sensor element according to claim 1, wherein a distance between a boundary surface and the dyeing section is 5 μm or more, the boundary surface being the boundary surface between the second ceramic layer and the solid electrolyte body.

4. The gas sensor element according to claim 1, wherein the signal lead part consists essentially of Pt.

5. The gas sensor element according to claim 1, wherein the signal lead part is formed by deposition.

6. The gas sensor element according to claim 1, wherein the signal lead part is formed on a section of the second ceramic layer in a width direction of the signal lead part.

7. The gas sensor element according to claim 1, wherein the signal lead part waves along a thickness region of 5 μm or more to 200 μm or less, as a thickness of a laminated direction of the second ceramic layer and the signal lead part.

8. A method for manufacturing a gas sensor the gas sensor comprising:
    an oxygen-ion conductive solid electrolyte body;
    a measuring electrode and a reference electrode provided respectively on a surface and another surface of the solid electrolyte body;
    a signal lead connected to the measuring electrode, the signal lead part extending to a base end side of the measuring electrode;
    a first ceramic layer covering the signal lead part from an opposing side to the solid electrolyte body; and
    a second ceramic layer mounted between the signal lead part and the solid electrolyte body, wherein:
any one metal or an alloy of more than one metal selected from a group consisting of Pt, Au, Ag, Pd, Rh, Ni and Ir, is laminated to an outer surface of the second ceramic layer by electroless plating in forming the signal lead part; and
the second ceramic layer has formed therein a dyeing section abutting the signal lead part,
the dyeing section comprising a part of the metal or the alloy that has been dyed in the second ceramic layer.

9. The method for manufacturing the gas sensor according to claim 8, wherein
Pt is laminated on the outer surface of the second ceramic layer by electroless plating to form the signal lead part.

10. The method for manufacturing the gas sensor according to claim 8, wherein
the second ceramic layer has a section, wherein the signal lead part is formed on the section of the second ceramic layer in the width direction of the signal lead part.

11. The gas sensor element according to claim 2, wherein a distance between a boundary surface and the dyeing section is 5 µm or more, the boundary surface being the boundary surface between the second ceramic layer and the solid electrolyte body.

12. The gas sensor element according to claim 2, wherein the signal lead part consists essentially of Pt.

13. The gas sensor element according to claim 3, wherein the signal lead part consists essentially of Pt.

14. The gas sensor element according to claim 2, wherein the signal lead part is formed by deposition.

15. The gas sensor element according to claim 3, wherein the signal lead part is formed by deposition.

16. The gas sensor element according to claim 2, wherein the signal lead part is formed on a section of the second ceramic layer in a width direction of the signal lead part.

17. The gas sensor element according to claim 3, wherein the signal lead part is formed on a section of the second ceramic layer in a width direction of the signal lead part.

18. The gas sensor element according to claim 2, wherein the signal lead part waves along a thickness region of 5 µm or more to 200 µm or less, as a thickness of a laminated direction of the second ceramic layer and the signal lead part.

19. The gas sensor element according to claim 3, wherein the signal lead part waves along a thickness region of 5 µm or more to 200 µm or less, as a thickness of a laminated direction of the second ceramic layer and the signal lead part.

20. The gas sensor element according to claim 4, wherein the signal lead part waves along a thickness region of 5 µm or more to 200 µm or less, as a thickness of a laminated direction of the second ceramic layer and the signal lead part.

* * * * *